United States Patent [19]

Vannelli et al.

[11] Patent Number: 5,335,293
[45] Date of Patent: Aug. 2, 1994

[54] PRODUCT INSPECTION METHOD AND APPARATUS

[75] Inventors: Anthony Vannelli; Thomas C. Madsen, both of Walla Walla, Wash.

[73] Assignee: Key Technology, Inc., Walla Walla, Wash.

[21] Appl. No.: 899,450

[22] Filed: Jun. 16, 1992

[51] Int. Cl.$^5$ .............................................. G06K 9/00
[52] U.S. Cl. ......................................... 382/17; 382/8; 382/1; 356/408; 209/581
[58] Field of Search ................. 382/17, 1, 8; 209/576, 209/577, 580, 581, 582; 356/407, 408, 237

[56] References Cited

U.S. PATENT DOCUMENTS

| | | | |
|---|---|---|---|
| 3,999,041 | 12/1976 | Scofield | 235/61 G |
| 3,999,047 | 12/1976 | Green | 235/151.3 |
| 4,238,768 | 12/1980 | Mitsuya et al. | 358/135 |
| 4,251,837 | 2/1981 | Janeway, III | 358/280 |
| 4,326,258 | 4/1982 | de la Guardia | 364/515 |
| 4,338,024 | 7/1982 | Bolz et al. | 356/23 |
| 4,439,789 | 3/1984 | Cahill | 358/256 |
| 4,543,660 | 9/1985 | Maeda | 382/34 |
| 4,567,610 | 1/1986 | McConnell | 382/18 |
| 4,574,393 | 3/1986 | Blackwell et al. | 382/17 |
| 4,590,606 | 5/1986 | Rohrer | 382/7 |
| 4,601,057 | 7/1986 | Tsuji et al. | 382/51 |
| 4,637,054 | 1/1987 | Hashim | 382/8 |
| 4,656,665 | 4/1987 | Pennebaker | 382/51 |
| 4,713,781 | 12/1987 | Brizgis et al. | 364/552 |
| 4,731,863 | 3/1988 | Sezan et al. | 382/51 |
| 4,742,551 | 5/1988 | Deering | 382/18 |
| 4,742,556 | 5/1988 | Davis, Jr. et al. | 382/51 |
| 4,742,557 | 5/1988 | Ma | 382/51 |
| 4,748,573 | 5/1988 | Sarandrea et al. | 364/551 |
| 4,764,971 | 8/1988 | Sullivan | 382/9 |
| 4,792,979 | 12/1988 | Nomura et al. | 382/54 |
| 4,804,842 | 2/1989 | Nakajima | 250/327 |
| 4,807,163 | 2/1989 | Gibbons | 364/555 |

(List continued on next page.)

FOREIGN PATENT DOCUMENTS

| | | | |
|---|---|---|---|
| 84103749.2 | 7/1984 | European Pat. Off. | H04N 7/18 |
| 86307 | 6/1986 | PCT Int'l Appl. | H04N 7/18 |
| 91536 | 6/1991 | PCT Int'l Appl. | H04N 7/18 |

OTHER PUBLICATIONS

Ye, Qin Zhang, et al. "On Minimum Error Thresholding and Its Implementations", Pattern Recognition Letter No. 4 Amsterdam, The Netherlands, (Apr. 7, 1988) pp. 201-206.

Primary Examiner—David K. Moore
Attorney, Agent, or Firm—Wells, St. John, Roberts, Gregory & Matkin

[57] ABSTRACT

Described herein is an automated quality inspection station for evaluating color component characteristics of a product. The inspection station includes a color video camera, for capturing video frames of product images, and a control system for analyzing those video frames. The control system is programmed to perform a reference calibration and then a sample calibration. During the reference calibration an operator identifies component type areas from a displayed reference frame of a typical product assortment. The control system calculates color value density curves from the identified areas. The density curves are then calibrated to each other by scaling each of the density curves by a scaling factor. The scaling factors can either be provided directly by the operator or default values can be calculated by the control system. Default scaling factor values are calculated by summing the product of the corresponding density curve and an overall histogram of a sample video frame over a range of color values. Individual pixels are classified as one of a plurality of component types according to the highest calibrated density curve at the pixels' color value.

60 Claims, 13 Drawing Sheets

U.S. PATENT DOCUMENTS

| | | | |
|---|---|---|---|
| 4,811,090 | 5/1989 | Khurana | 358/93 |
| 4,812,904 | 3/1989 | Maring et al. | 358/107 |
| 4,856,528 | 8/1989 | Yang et al. | 128/653 |
| 4,868,883 | 9/1989 | Chen | 382/1 |
| 4,901,258 | 2/1990 | Akiyama | 364/577 |
| 4,907,282 | 3/1990 | Daly et al. | 382/9 |
| 4,941,192 | 7/1990 | Mishima et al. | 382/54 |
| 4,945,478 | 7/1990 | Merickel et al. | 364/413.22 |
| 4,951,825 | 8/1990 | Hawkins | 209/558 |
| 4,955,067 | 9/1990 | Shimura | 382/62 |
| 4,959,869 | 9/1990 | Hongo | 382/51 |
| 4,962,540 | 10/1990 | Tsujiuchi et al. | 382/17 |
| 4,972,493 | 11/1990 | Chemaly | 382/8 |
| 4,975,972 | 12/1990 | Bose et al. | 382/8 |
| 4,977,605 | 12/1990 | Fardeau et al. | 382/51 |
| 4,979,225 | 12/1990 | Tsujiuchi et al. | 382/17 |
| 4,992,949 | 2/1991 | Arden | 209/582 |
| 5,046,118 | 9/1991 | Ajewole et al. | 382/51 |
| 5,048,095 | 10/1991 | Bhanu et al. | 382/9 |
| 5,060,279 | 10/1991 | Crawford et al. | 382/14 |
| 5,060,290 | 10/1991 | Kelly et al. | 382/18 |
| 5,085,325 | 2/1992 | Jones et al. | 209/580 |

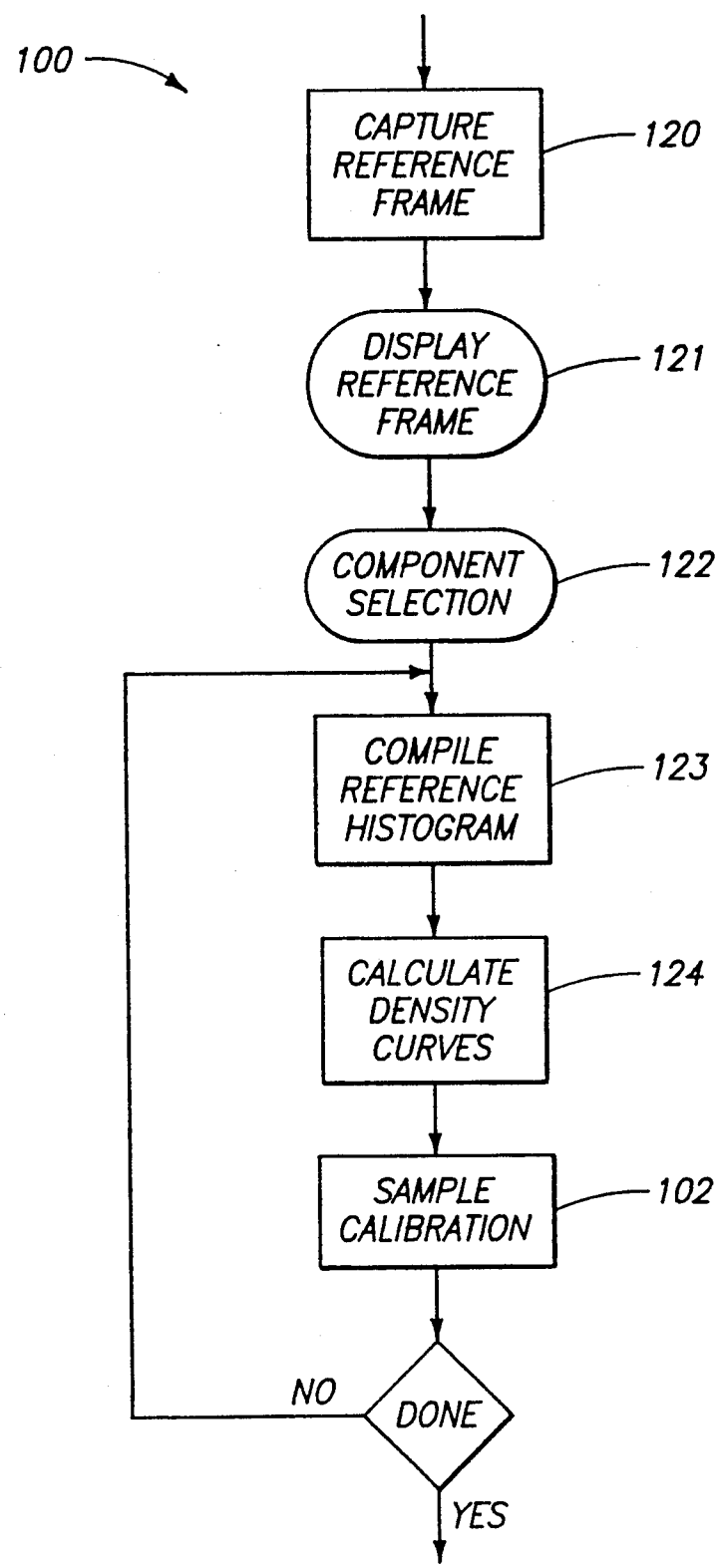

PRODUCT INSPECTION METHOD AND APPARATUS

TECHNICAL FIELD invention relates to methods and apparatus for inspecting food products and other products or items whose quality can be visually ascertained; for classifying component areas of such products or items; and for setting process parameters of in-line processing equipment based on such classifications.

BACKGROUND OF THE INVENTION

Pixel classification is sometimes referred to as segmentation, in which various segments of an image are identified as belonging to individual product component types. Pixel classification is commonly used in quality control or product inspection applications, particularly in the food products industry, in order to distinguish between acceptable and defective product.

Food products are often graded by their appearance. Green beans, for instance, are expected to be a uniform shade of green. Defects within a single green bean might be formed by white, brown, black, or other discolored areas. It is desirable to detect green beans having such defective areas, and to separate them from green beans without such defects. It may also be desirable to quantify the defective areas, and to reject as defective only those green beans having more than a specified area of any certain type of defect.

Before automated product inspection can take place, an image of the product must be captured in a form which is meaningful to a computer or data processor; a form in which the image is represented by a series or array of numbers. Electronic video systems do this by dividing an image into a number of discrete picture elements or "pixels." Each pixel has an associated color value, representing the hue and intensity of that portion of the image which corresponds to the pixel.

In a monochrome or black-and-white video system, the color value is specified by a single variable which ranges from 0 to n. The color value in such a case represents the absolute light intensity of the image area corresponding to the pixel. A color value of 0 corresponds to black, and a color value of n corresponds to white. Intermediate color or intensity values correspond to progressing levels of grey.

In a color video system it is necessary to record intensities for at least two different ranges of colors. Three different color ranges, designated red, green, and blue are typically used. Thus, a single color value in a color video system might be specified by three or more discrete variables or intensity values, r, g, and b, corresponding to intensities of red, green, and blue.

In segmenting a video image, it is necessary to classify each possible color value as one of a plurality of component types. A component type is defined as an area of the product representing a single quality classification such as "acceptable" product, "white defect" product, "brown defect" product, or another classification, depending on the nature of the product. In practice, it is desirable to define a number of such quality classifications corresponding not only to visually identifiable product areas, but also to areas representing foreign objects such as rocks or wood. Segmenting the video image is often the first and most critical step in a detailed image analysis which includes many subsequent analytical steps.

In a monochrome system, in which each pixel is represented by a color value having only one intensity value, it is common to set one or more thresholds for purposes of color value or pixel classification. The relationship of each pixel's color value to the thresholds determines that pixel's classification. Because the color value is single-dimensioned, e.g., a function of a single variable, the operator is able to easily conceptualize the thresholds and vary them to obtain the desired segmentation results. Varying the single-dimensioned thresholds is a simple matter of increasing or decreasing their values.

Pixel classification becomes somewhat more difficult when the color value has two or three variables or dimensions, such as in a color video system having r, g, and b intensity values. Simple thresholds, if used, would need to be set for each of the three dimensions. Not only would such thresholds be difficult for an operator to conceptualize, but the number of variables would make meaningful and proper adjustment nearly impossible. In addition, simple thresholds allow specification of only a rectangularly shaped space in the three-dimensional space defined by the possible color values, while actual component areas usually contain color values forming irregular shapes within the three-dimensional color value space. Therefore, color analysis systems generally require more sophisticated methods of pixel or color value classification than are used with black-and-white systems.

One approach to color image classification, used in a diamond inspection apparatus, is described in U.S. Pat. No. 4,951,825 to Hawkins et al., entitled "Apparatus for Classifying Particulate Material." The Hawkins patent describes a "learning" process in which one class at a time of pre-sorted diamonds are introduced into the machine. The machine stores the color values obtained during the learning process and subsequently compares color values in sample diamonds with the stored values to determine the closest match.

The method described by Hawkins et al. might be suitable when it is not necessary to detect specific features occurring within a single image. The method is not sufficient, however, when component types contained within the same image must be differentiated from each other, or when it is required to detect the presence of small component types within larger articles.

A more suitable approach for classifying a number of component types, all contained within the same image, is described in U.S. Pat. No. 4,807,163 to Gibbons, entitled "Method and Apparatus for Digital Analysis of Multiple Component Visible Fields." Gibbons describes segmenting an image of a human scalp to quantify hair loss.

In the Gibbons method, subareas of a visual image, each containing only a single component type (bald or not bald), are initially identified or selected by an operator from a sample image. A histogram is then compiled for each identified sub-area, and mean intensity values are determined for each component type based on the histogram. The intensity value for each pixel is then compared to the mean intensity values. If the pixel intensity value falls within a predetermined range of any component mean intensity value, it is classified as that component type. The pixels are then counted to determine the number of pixels classified as bald.

In an alternative embodiment, Gibbons compares the mean intensity value for two component types to determine an average intensity value. This average intensity value is then used as a threshold, with higher values being classified as one component type and lower values being classified as the other component type.

Gibbons does not address the problem of setting thresholds in the three-dimensional space of a color analysis system. In fact, the prior art has to this date failed to adequately address the problem of accurately setting classification parameters in a color system. Most prior art systems are directed to single color systems or are limited to distinguishing between two component types. Many of these systems also require operator intervention prior to analyzing each image.

The prior art classification methods are not easily adaptable to color systems in which pixels are represented by more than one variable or intensity value. For instance, it is not clear in the Gibbons disclosure how intensity value comparisons could be made in each dimension of a three-color system. Even if the Gibbons methods were adaptable to color systems, the simple thresholds described would make it impossible to set accurate boundaries for component types occupying irregular three-dimensional spaces.

In addition, the prior art, including the Gibbons patent, does not adequately account for cases in which the component types have overlapping histograms—when a specific color value occurs in more than one component type. In such cases, it is necessary to determine the proper component type classification for each color value. The Gibbons analysis arbitrarily selects a threshold based on mean histogram values. This threshold has no correlation to the desired classification priority.

The invention described below provides means and methods for classifying pixels and their color values as one of many component types, taking into account relative classification priorities and other factors, and resulting in more reliable classification. In addition, the methods described below adapt themselves automatically to changing product loads and conditions.

BRIEF DESCRIPTION OF THE DRAWINGS

Preferred embodiments of the invention are described below with reference to the accompanying drawings, in which:

FIG. 15 is an alternative embodiment reference calibration in accordance with the methods of this invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts." U.S. Constitution, Article 1, Section 8.

Described below is an automated quality inspection device or color product analyzer for identifying and evaluating visual or optical component characteristics of food products or other products whose quality can be visually ascertained. The product analyzer provides a method of classifying pixels and pixel color values according to their component types. Such classification is then used in subsequent analytical steps as desired. In the preferred embodiments described below, the classifications are used in calculating statistical quality control data regarding visual characteristics of multiple product samples. In general, such calculations include segmenting visual images into their constituent component types. Another possible use for such classification is in setting classification parameters for in-line optical sorting machines, in which segmentation is sometimes not involved.

Figure 1:
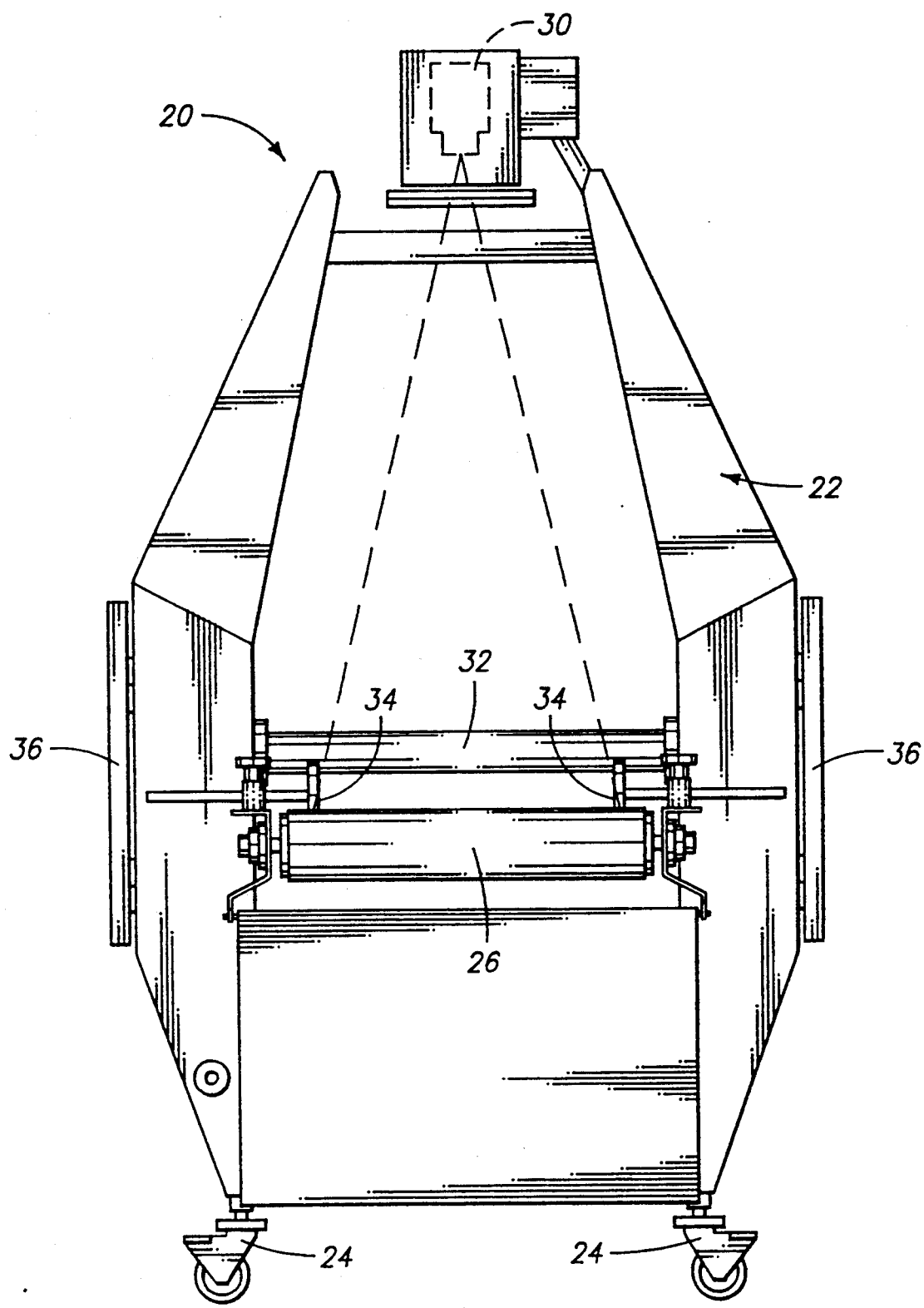
FIG. 1 is an end view of a preferred embodiment of a color product analyzer in accordance with the invention.
Figure 2:
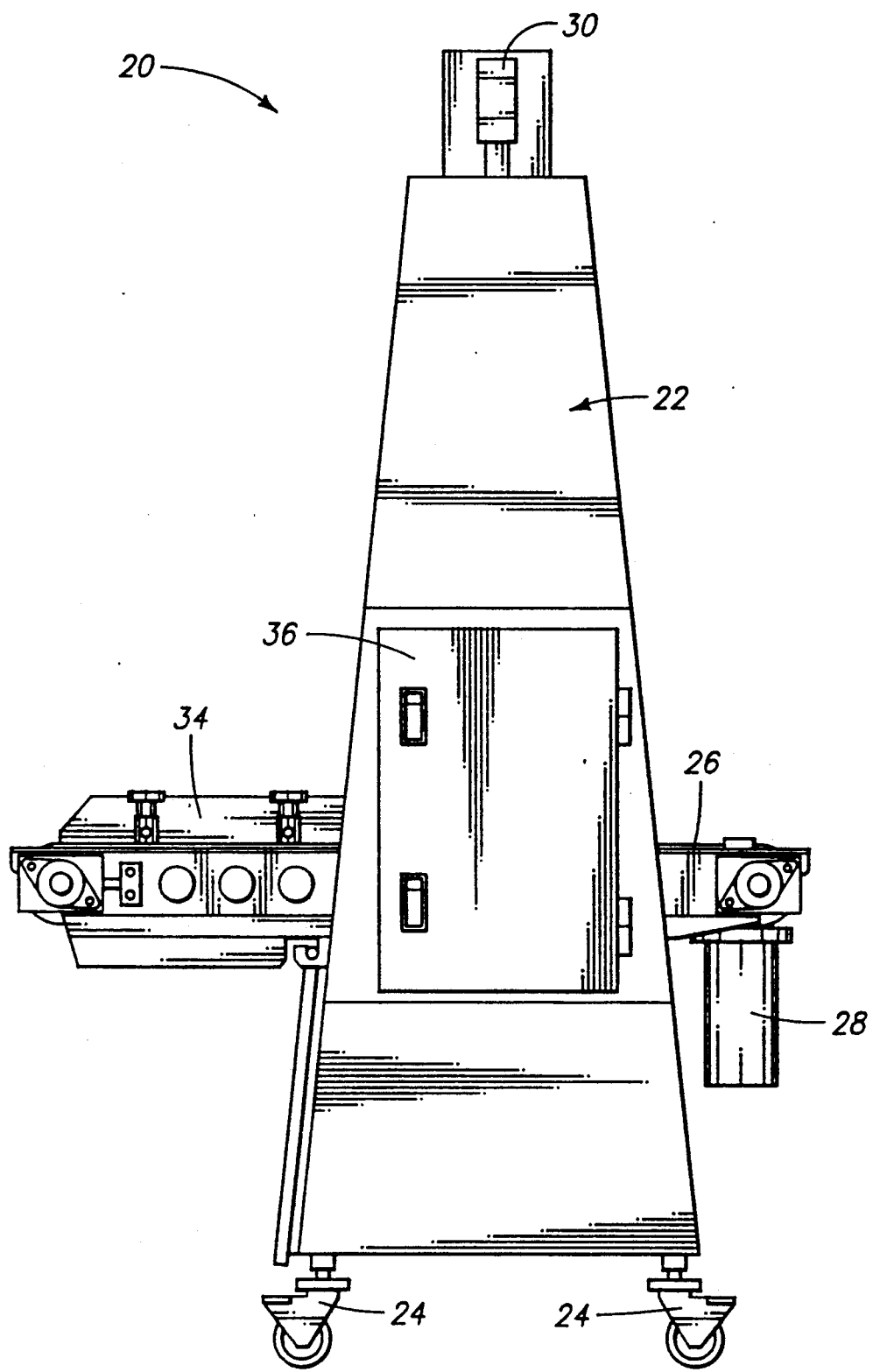
FIG. 2 is a side view of the product analyzer shown in FIG. 1.

FIG. 1 and 2 show a preferred embodiment of an automated quality inspection device or station in accordance with the invention, generally designated by the reference numeral 20. Inspection station 20 includes a frame 22 supported by casters 24. A product conveyor belt 26 runs longitudinally through frame 22. A conveyor motor 28 is mounted to frame 22 to power conveyor belt 26. Conveyor belt 26 forms a product sample surface for supporting product which is to be inspected.

A camera 30 is positioned relative to the optical inspection surface formed by conveyor belt 26 to produce video frames or images of the supported sample product. Each video frame contains an array of pixels or color values. Each pixel represents a corresponding area of a sample product image.

Camera 30 produces a video signal with color values representing each pixel. Each color value is specified by at least one variable to indicate the color, shade, or intensity of the corresponding pixel. In the preferred embodiment, each color value is defined by three variable image intensity values: red (r), green (g), and blue (b). The methods of the invention are particularly appropriate in such a system, where the color values are specified by at least two variables.

Inspection station 20 uses a 3-color line scan camera which produces repeated linear scans across the surface of a belt, each scan being representative of optical characteristics of the product. A succession of linear scans can be accumulated to form a two-dimensional array of pixels representing a two-dimensional visual image.

Camera 30 utilizes an optical transducer or sensing device (not shown) which contains three rows of light sensitive sensors. Each row is sensitive to a different range of optical wavelengths, so that each row corresponds to one of the three intensity variables. Since the rows are spaced from each other in the direction of product flow, they are each responsive to a different transverse line across conveyor belt 26. The rows are logically shifted, subsequent to image capture, to align them relative to each other.

Inspection station 20 also includes a pair of fluorescent light tubes 32 for illuminating product on conveyor belt 26. A pair of product guides 34 are adjustable to guide product within the line of sight of camera 30 (indicated by dashed lines). Electronic control circuits are housed within frame 22 behind doors 36.

Figure 3:
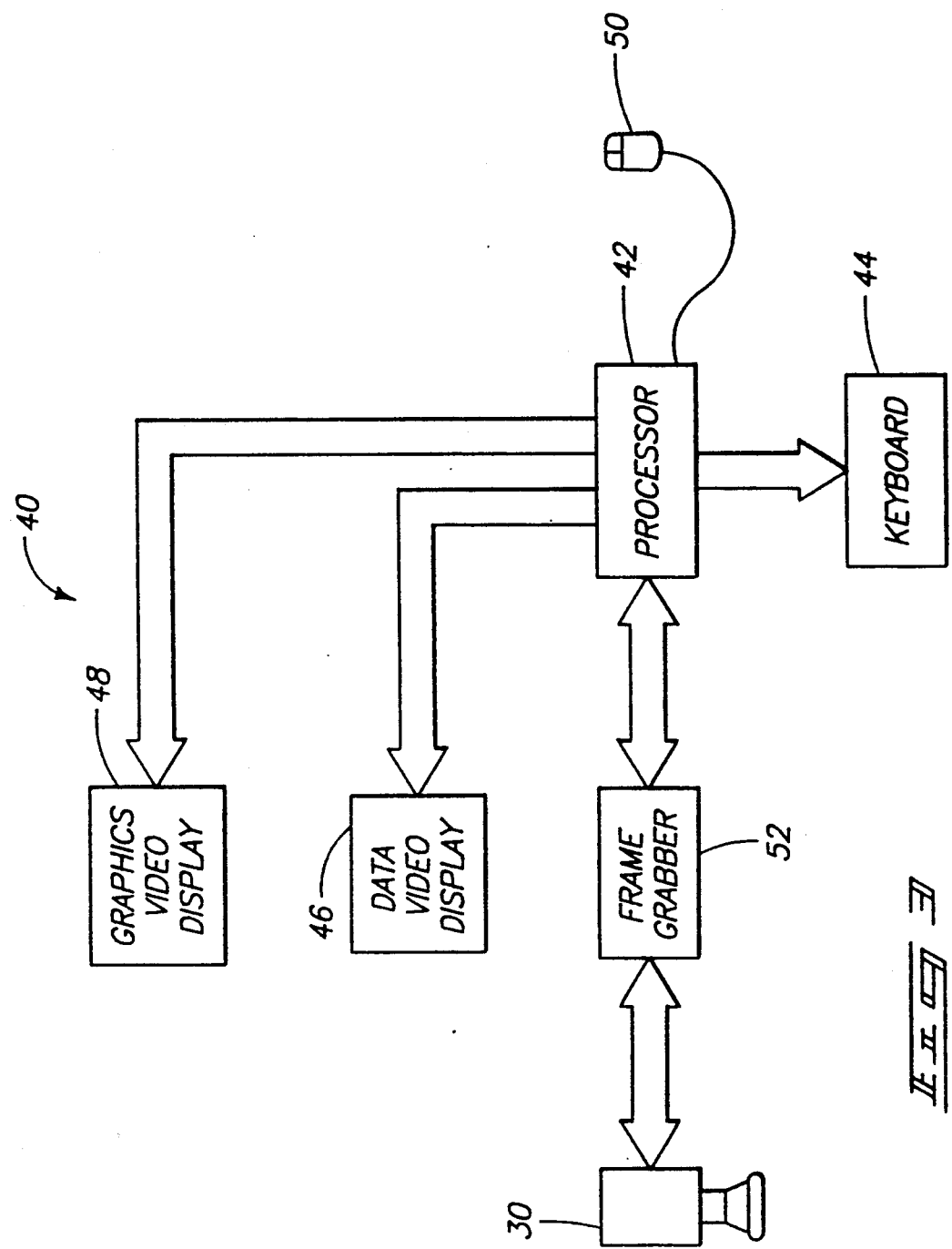
FIG. 3 is a schematic block diagram of a control system which is part of the color product analyzer shown in FIG. 1.

FIG. 3 shows a control system 40 which forms a part of inspection station 20. Control system 40 is connected to control and receive the images or video frames from camera 30. It comprises a processing means or data processor 42, an associated keyboard 44, a data video display monitor 46 for displaying data, a graphics video display monitor 48 for displaying segmented and unsegmented video frames, and an input device 50 such as a light pen or mouse for allowing an operator to select sub-areas from graphics video display 48 and to otherwise provide instructions to data processor 42.

A frame grabber 52 is connected to camera 30 and receives the video signal produced by camera 30. It contains means for capturing and storing multiple scans of camera 30, the multiple scans comprising a two-dimensional video image of product flowing beneath camera 30. A variety of suitable frame grabber boards, adaptable to a variety of video cameras, are widely available from various manufacturers.

Data processor 42 is operably connected to control and receive video frames from camera 30 and frame grabber 52. It is also connected to display monitors 46 and 48 and to mouse 50. Data processor 42 is a general purpose computer such as an IBM-compatible computer having an Intel 80486 microprocessor or CPU, as well as appropriate volatile and non-volatile memory. The selection of data processor 42 is dictated primarily by its processing capacity and the time constraints imposed by the particular application.

Data processor 42 is programmed by conventional means to perform the operations and control functions described below. It communicates and receives instructions from an operator through keyboard 44, mouse 50 and video display monitors 46 and 48.

Alternative embodiments of both the electronic and mechanical hardware are of course possible without departing from the principles of this invention. In general, some means for obtaining a video frame of a product sample is required. Many different methods of obtaining such a video frame are commonly available and used. For instance, a two-dimensional video camera, rather than a line scan camera, could advantageously be provided for simultaneously capturing an entire video frame. Such a two-dimensional camera would in most applications be equally preferable to the line scan camera described above. If using such a camera it would be possible, although not required, to provide a stationary inspection surface rather than a conveyor belt. The primarily advantage of a conveyor belt support surface is that it allows placement of the inspection station in-line with a continuous product flow so that inspection may be made without interrupting the product flow.

In operation, a continuous flow of product passes beneath camera 30 on conveyor belt 26. Control system 40 is programmed to periodically capture a video frame representing a two-dimensional video image of the product passing below camera 30. The control system analyzes each image and produces a quality control report based on the results of this analysis.

In analyzing video images, inspection station 20 segments images on the basis of color value differentiation—each pixel is classified into a component type according to its color value. Each color value is therefore classified as "belonging" to one, and only one, component type classification. Pixels are classified in accordance with the classification of their color values.

The various possible component types are defined prior to classification in response to operator instructions. For instance, a particular product might have classifications corresponding to "white defect," "brown defect," "light acceptable product," "dark acceptable product," "rocks," and "other." Component types may also exist for "background," and "unidentified" areas.

Figure 4:
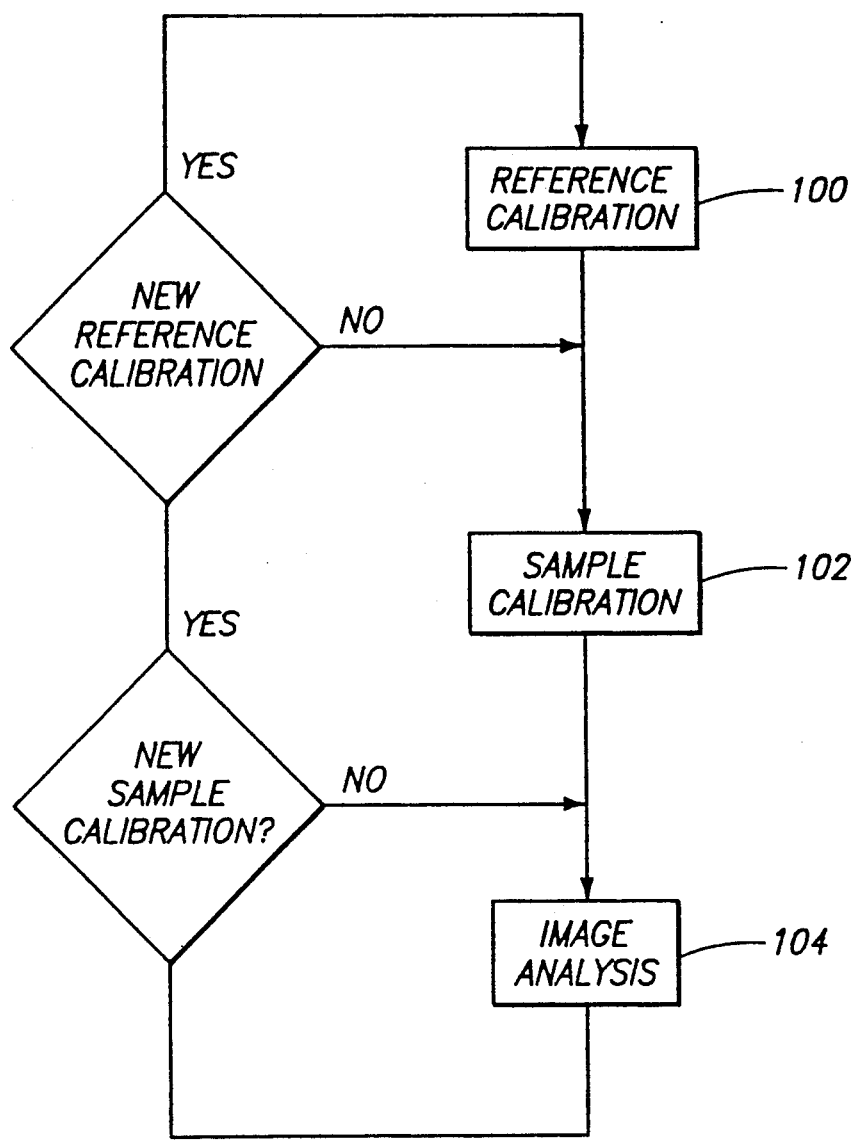
FIG. 4 is a simplified flow chart showing preferred methodical steps in accordance with the invention.

FIG. 4 is a flow chart showing operation of the apparatus and the overall methodical steps in accordance with the preferred embodiment of the invention. Control system 40 is programmed to initially perform a reference calibration 100, followed by a sample calibration 102. Image classification and analysis 104 follows the calibration steps.

Reference calibration 100 allows the operator to identify the component types, from a reference video image of actual product, into which pixels are to be classified. Sample calibration 102 is an analytical step, based on a sample video image of actual product, in which color value classification criteria are determined. Image analysis 104 includes classifying image pixels according to their color value classifications. It also typically includes segmenting video frames based upon the component type classifications of their pixels and further steps such as shape analysis which are not within the scope of this invention. The image analysis step 104 is reiterated for subsequent video images. Reference calibration 100 and sample calibration 102 are repeated as desired or as instructed by an operator.

Reference frame calibration 100 generally requires operator intervention and is therefore performed only infrequently, for example when setting up for a new or different type of product. Sample frame calibrations, on the other hand, are not dependent on operator input and may therefore be performed along with every sample frame. However, practical constraints such as available processing time and speed will often dictate that sample frame calibrations be performed only periodically at an operator's instruction.

During reference frame calibration 100 the control system captures a reference video frame. A reference frame is a video frame representing an image of a typical product assortment. The operator then specifies portions of individual component types within the reference video frame. Reference calibrations can be repeated periodically if needed, although it is contemplated that the need for repeating the reference calibration will arise only rarely, usually when introducing a new product or product batch to the analyzer.

During subsequent sample frame calibration 102, the control system captures a sample frame. The control system is programmed to derive relative component type probability curves from the identified portions of the individual component types, preferably by comparing the color values of the identified portions to the color values of the overall sample video frame. The control system then classifies individual color values as single component types according to the highest relative component type probability for each individual color value.

The sample frame can be the same frame as the reference frame, or it may be captured subsequently to the reference frame. It may be a frame which is to be analyzed or a frame which is to be used solely for calibration purposes, with analysis being performed on subsequent frames.

During the image analysis step 104, pixels are classified based on the classifications of their color values (as established in sample calibration 102). The image is segmented accordingly and further analyzed as required by the particular application. Subsequent images are analyzed without any further requirement for calibration steps. If desired, however, the sample calibration step can be performed prior to analyzing each image.

Figure 5:
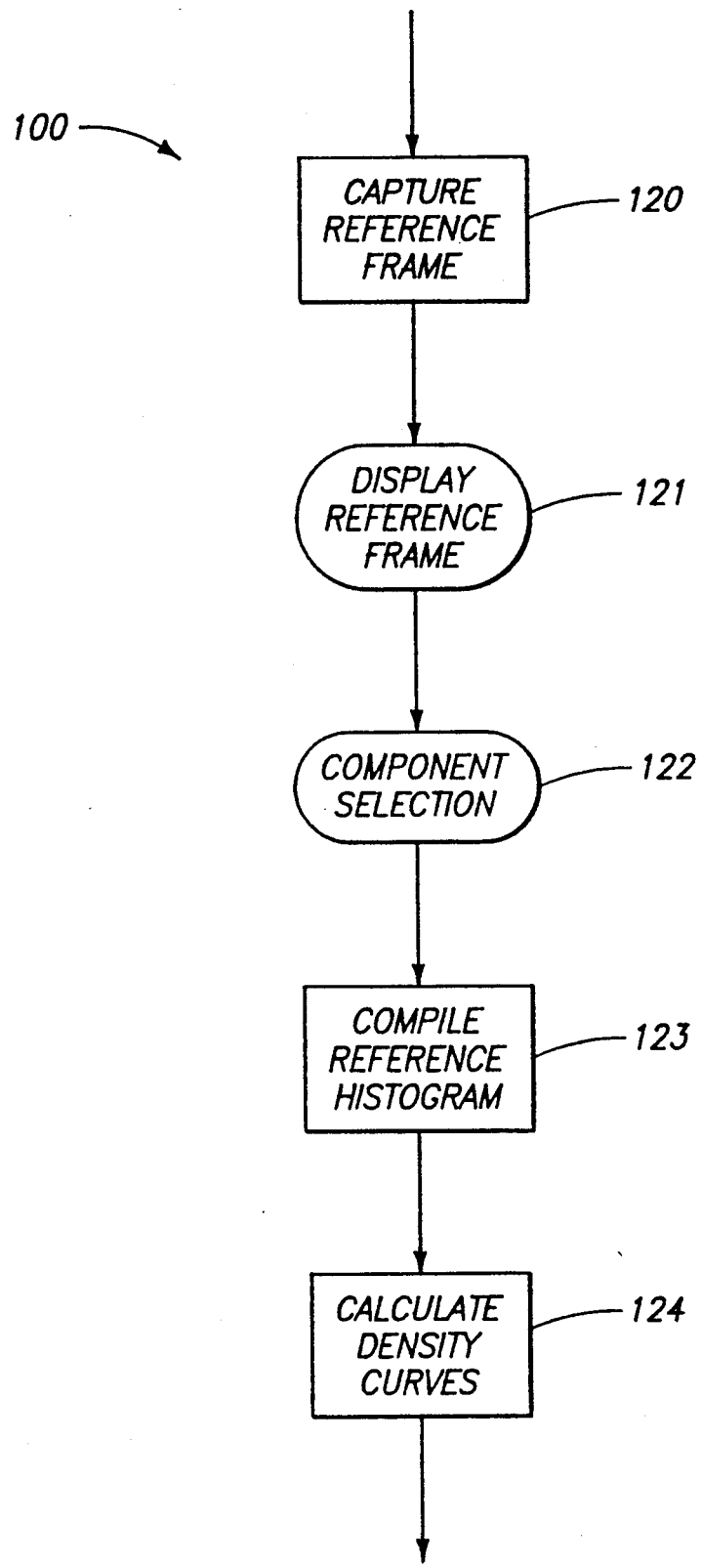
FIG. 5 is simplified flow chart showing the methodical steps of a reference calibration in accordance with the methods of this invention.

FIG. 5 shows steps for performing a reference frame calibration 100 in accordance with the methods of this invention. Reference frame calibration 100 includes the following steps, performed by control system 40: (a) capturing a reference video frame of a representative product sample (step 120); (b) displaying the reference video frame on graphics video display 48 (step 121); (c) allowing an operator to identify portions of individual component types within the reference video frame (step 122); (d) compiling reference or component histograms of color values occurring within the identified portions of individual component types (step 123); and (e) calculating reference color value density curves from the component histograms (step 124).

Figure 6:
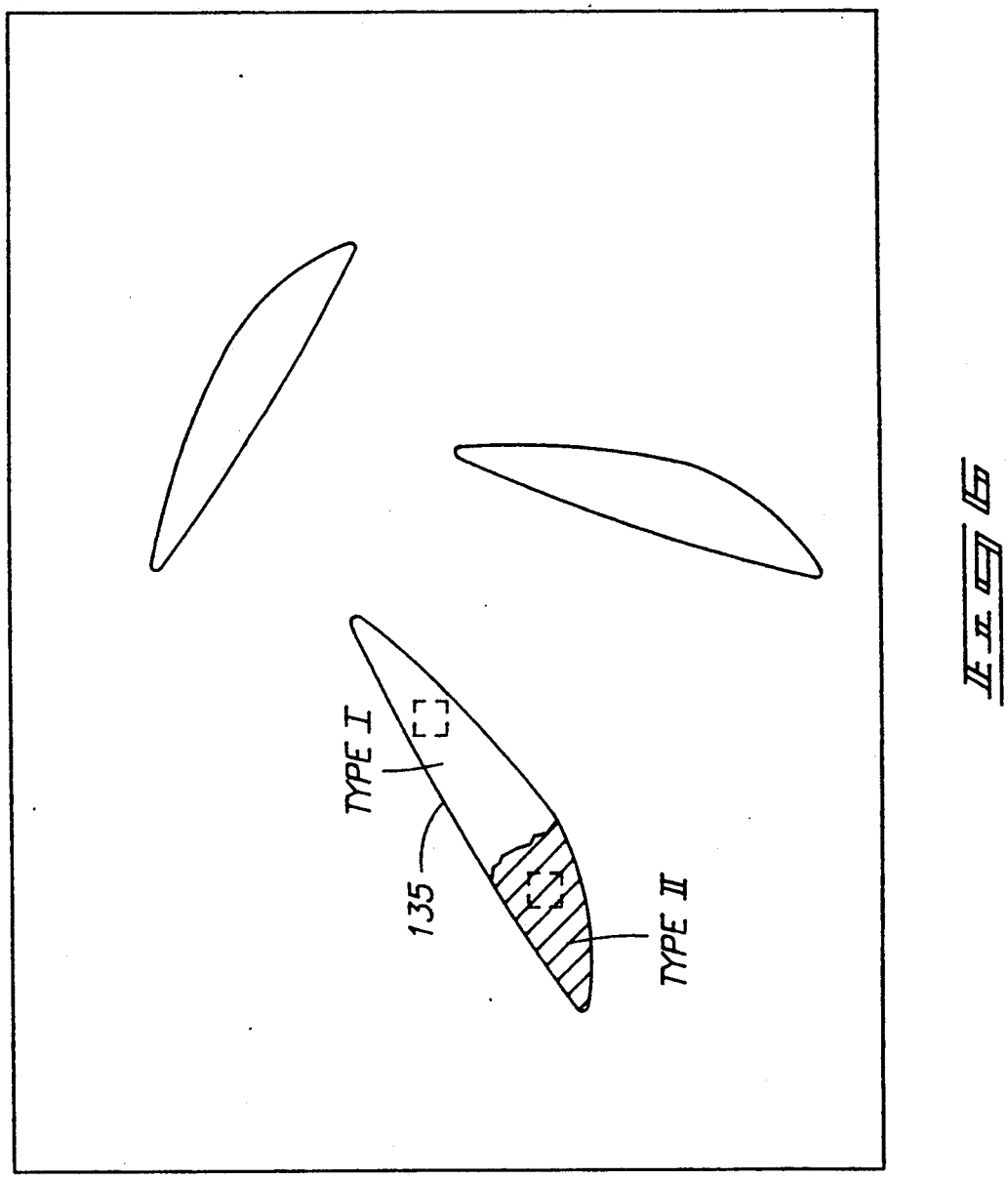
FIG. 6 is a simplified illustration of a reference video frame.

FIG. 6 shows a simplified reference video frame 130 which has been captured and displayed on graphics video display monitor 48. A green bean 135 is shown in FIG. 6 as an example of an article which is to be analyzed or segmented. To simplify the explanation, assume that green bean 135 contains only two component types: type I and type II. Type I represents acceptable or desirable areas of the green bean while type II represent areas of the article having undesirable or unacceptable visual characteristics. While FIG. 6 shows green bean 135 as two discrete areas, the actual representation would show only slight or gradual color variations from one component type to another.

For further simplification, the following discussion is presented in terms of a single-color or monochrome system, in which each color value is represented by a single variable. The methods presented, however, are particularly applicable to color systems in which color values are represented by a plurality of variables and in situations where it is desired to identify more than two component type areas. The methods presented are directly applicable to such situations.

The operator is instructed to identify areas on the display corresponding to each component type which is to be identified. Mouse 50, keyboard 44, and graphic video display monitor 48 form component selection means which are operably connected to processor 42 for allowing the operator to identify portions of individual component types within reference video frame 130. The operator can select individual pixels or an area of pixels. The rectangular, dashed boxes indicate areas which the operator has identified as being portions of the two component areas.

The operator identifies component areas by selecting individual reference pixels or by tracing an area of reference pixels. The control system is programmed to highlight or otherwise indicate selected reference frame pixels or areas. The operator in this step need not identify all component areas of each type, nor is it necessary to accurately trace the exact perimeters of the component areas selected. All that is necessary is to highlight at least nine or ten reference pixels representative of each component type. Ultimate accuracy is of course enhanced if relatively large areas or numerous instances of each component type are selected. Nevertheless, the methods of this invention will achieve a high degree of accuracy even when only small component areas are identified.

After operator selection, the identified component areas define a number of reference pixels for each component type. Processor 42 is programmed to compile reference histograms from these pixels corresponding to the component types. Reference histograms indicate the number of occurrences of each possible color value within the identified portions of the component types.

Figure 7:
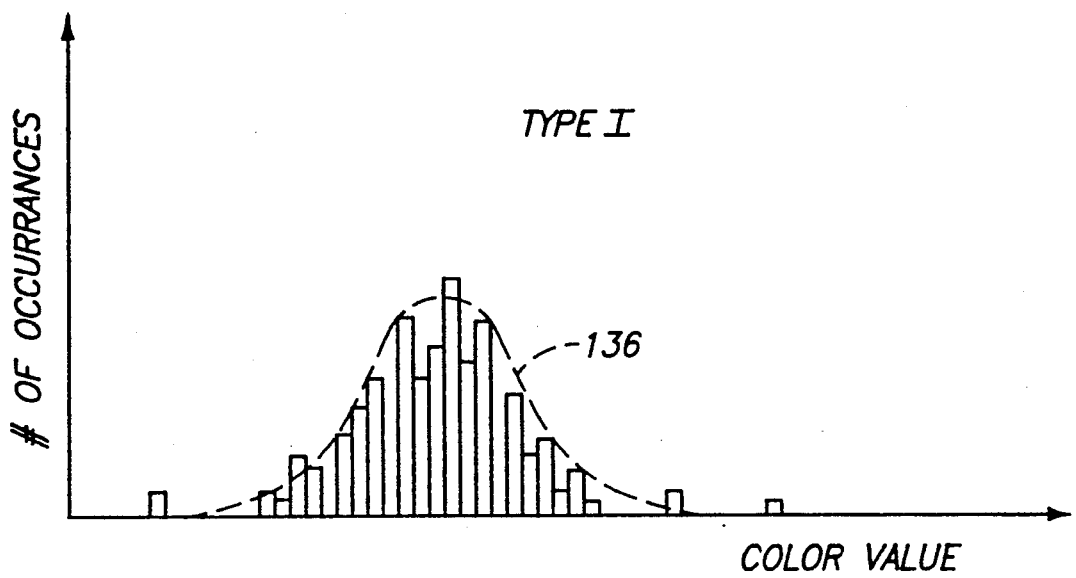
FIG. 7 is a simplified, single-dimensional, histogram of color values occurring within the type I area of FIG. 6.
Figure 8:
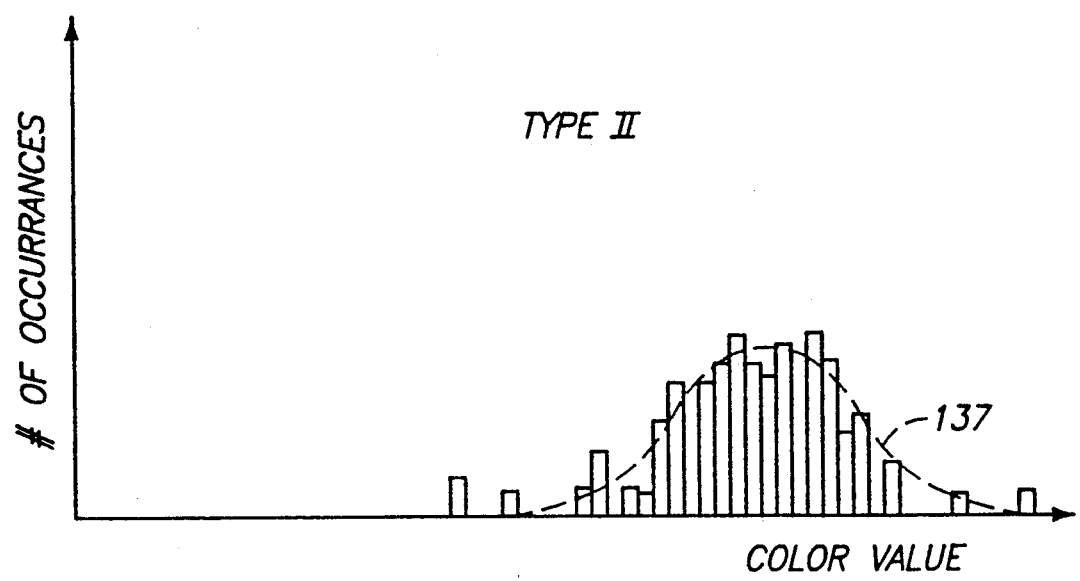
FIG. 8 is a simplified, one-dimensional histogram of color values occurring within the type II area of FIG. 6.

FIGS. 7 and 8 show reference histograms corresponding to the identified portions of component types I and II of FIG. 6. Such histograms are typically incomplete to the extent that not all color values were included in the identified portions of the component types. In many cases, not all possible color values for a component type are even present in the reference frame—subsequent video frames may contain additional color values which should be classified as the component type. Further, identified samples may contain localized anomalies not generally representative of the corresponding component type.

To account for these deficiencies, processor 42 is programmed to calculate color value density curves, also referred to as reference curves, from the reference histograms for each component type. Each reference curve is a continuous function which is fit to the corresponding reference histogram using a least square analysis. The calculated density or reference curves represent, for each component type, an approximation of the statistical distribution of color values within the component type.

The least square analysis utilizes a set of functions known as Hermite polynomials, weighted by a Gaussian weighting function. Utilizing the Hermite polynomials simplifies the least square analysis as described below.

The gaussian weighting function E(x) for a given reference histogram is given by the following equation:

$$E(x) = \frac{1}{\sqrt{\sigma\sqrt{\pi}}} \exp\left(\frac{-x^2}{2\sigma^2}\right)$$

where $\sigma$ is the standard deviation of the reference histogram. The first four orders of Hermite polynomials ($P_0$ through $P_3$) are used in the least square analysis:

$$P_0(t)=1 \quad P_1(t)=2t \quad P_2(t)=4t^2-2 \quad P_3(t)=8t^3-12t$$

The Hermite polynomials $P_0$ through $P_3$ are weighted and normalized as follows prior to being fit to the reference histogram:

$$N_0(x) = E\left(\frac{x-u}{\sigma}\right)$$

$$N_1(x) = \frac{-1}{\sqrt{2}} P_1\left(\frac{x-u}{\sigma}\right) E\left(\frac{x-u}{\sigma}\right)$$

$$N_2(x) = \frac{1}{\sqrt{8}} P_2\left(\frac{x-u}{\sigma}\right) E\left(\frac{x-u}{\sigma}\right)$$

$$N_3(x) = \frac{-1}{\sqrt{86}} P_3\left(\frac{x-u}{\sigma}\right) E\left(\frac{x-u}{\sigma}\right)$$

where u is the mean color value of the reference histogram. The normalizing factors preceding the polynomial functions ensure that the functions are normalized to each other—that their integrals are equal to one.

Weighted and normalized polynomials $N_0$ through $N_3$ are calculated for each of the three color value dimensions or variables, r, g, and b, yielding 12 polynomial functions.

The orthogonal nature of the weighted polynomials simplifies subsequent calculations. Sixty four polynomial coefficients are therefore calculated as follows:

$$C_{i,j,k} = \sum_{r=0}^{l} \sum_{g=0}^{m} \sum_{b=0}^{n} \sqrt{H_m(r,g,b)} \, N_i(r) \, N_j(g) \, N_k(b)$$

where i, j, and k vary from 0 to 3, representing the four orders of Hermite polynomials. H(r,g,b) is the reference histogram for which a density curve is being calculated.

The reference function or curve D(r,g,b) is then calculated directly, using coefficients $C_{i,j,k}$, as follows:

$$D(r,g,b) = \left(\sum_{i=0}^{3} \sum_{j=0}^{3} \sum_{k=0}^{3} C_{i,j,k} \, N_i(r) \, N_j(g) \, N_k(b)\right)^2 F$$

where F is a normalization factor which is calculated to ensure that the integral of the square of each density curve is equal to one, or that $$\sum_{r=0}^{l} \sum_{g=0}^{m} \sum_{b=0}^{n} (D(r,g,b))^2 = 1$$

The function fitting steps described above, when performed only in a single dimension, result in reference density curves 136 and 137, shown by dashed lines in FIGS. 7 and 8, corresponding to the type I and type II reference histograms, respectively. The particular steps described have the advantage of automatically adapting to reference histograms having varying widths or standard deviations; the width of the weighted Hermite polynomials varies with the reference histograms' standard deviation. This produces density curves which quite accurately fit their corresponding reference histograms. In many cases, such as when a histogram contains a minimal number of samples, only two or three orders of the weighted Hermite polynomials need be used in the least square analysis.

Figure 10:
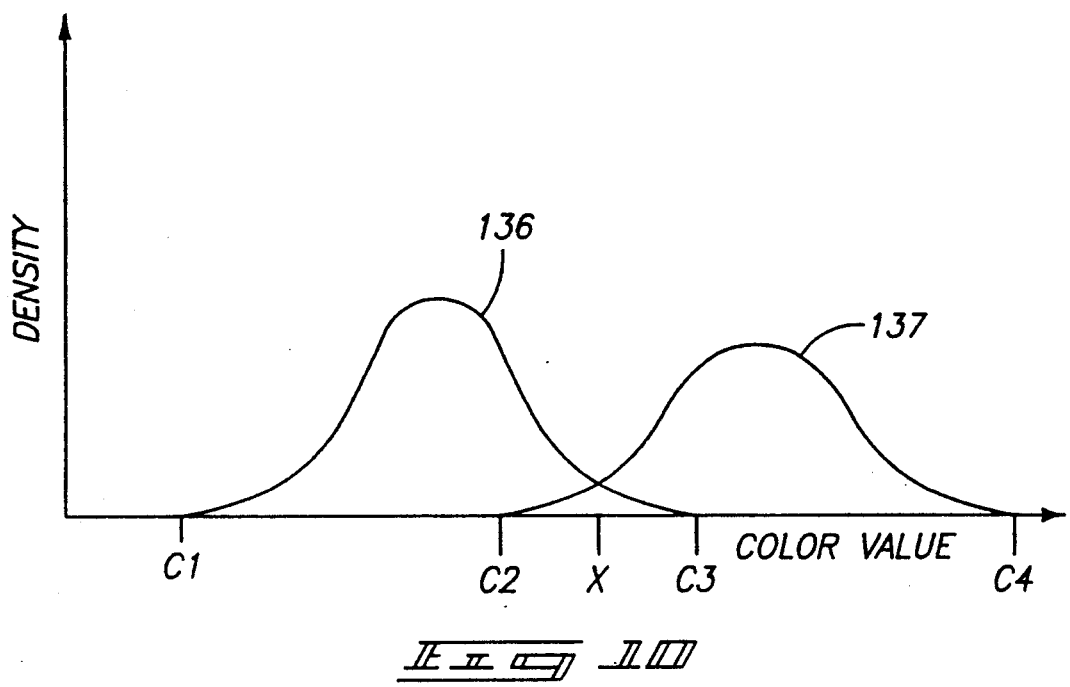
FIG. 10 shows color value density curves corresponding to the type I and type II areas of FIG. 6.

FIG. 10 shows density curves 136 and 137 superimposed over each other. The curves indicate that color values in the range of C1 to C3 have a finite statistical probability of occurring in type I components. Color values in the range of C2 to C4 have a finite statistical probability of occurring in type II components. An overlap occurs between C2 and C3, with the color values in that range being likely to occur in both type I and type II component types.

Because of overlaps such as illustrated in FIG. 10, pixel classification based solely on color value discrimination will of mathematical necessity involve uncertainties and a certain number of erroneous classifications. For instance, a color value of X, within an overlap of component type color values, might occur in either of the type I and type II component types. In more complex situation, a given color value might legitimately occur in several component types. In assigning such a color value to a component type, previous methods have set arbitrary "thresholds," or have ignored the possibility of a color value occurring in an overlap area. The methods of this invention, however, provide a logical and meaningful determination of the desired classification based on relative component type probabilities as calculated or set by an operator.

A general feature of this invention includes determining the probability of any single color value occurring in any single component type, as opposed to that same color value occurring in any other component type. The reference curves do not indicate this probability, since they show only the relative distribution of color values within a single component type. The density curve magnitudes are dependent upon the size of the identified portions of the component types and upon the normalization factors used in calculating the density curves. Therefore while the shape of the reference curves are meaningful, their overall magnitudes are arbitrarily set. The density curves do not predict the relative probability of a single color value occurring in one or another of the component types.

For instance, component type I occurs much more frequently in green bean 135 than does component type II. Therefore, color values corresponding to component type I are also more likely to appear in any video frame of green beans than are color values corresponding to component type II. The density curve magnitudes do not represent this fact.

Further methods of this invention include allowing an operator to specify how the uncertainties created by color value overlaps are resolved. The methods thus provide a logical and consistent basis upon which to base classification decisions regarding color values within component type overlaps. Such methods include scaling or calibrating the reference density curves relative to each other to make them more meaningful in relation to each other. This scaling is performed in a sample calibration step by appropriately multiplying the reference curves.

In a first embodiment of a sample calibration the operator is allowed to specify and adjust probability scaling factors which are then used to scale the reference curves. The scaling results in probability curves, wherein each probability curve represents the probability of any single color value occurring in any single component type relative to any other component type. Each pixel is classified as the component type having the highest relative probability at the pixel's color value, according to the probability curves. The operator can view on the video display monitor the resulting image segmentation while adjusting the probability scaling factors, and can therefore set the scaling factors to achieve the desired discrimination between various component types. The operator also sets a minimum probability threshold. Color values having probabilities only beneath this threshold are classified as "other" or "unidentified," rather than as any of the component types specifically identified by the operator.

For instance, in a particular application it might be desired to identify all pixels which are at all likely to be of a first component type—even if it results in erroneously including pixels of a second component type in the first component type. In other words, the operator can specify that overlap uncertainties be resolved in favor of a first component type classification. To do this, the operator increases the probability scaling factor for the first component type to place a relatively higher importance or cost on the first component type, even at the expense of erroneously identifying some second component type pixels as the first component type.

In a second, more preferable embodiment of a sample calibration, default values for the density scaling factors are calculated automatically, and the operator specifies probability multipliers corresponding to each component type. The data processor is programmed to adjust each default density scaling factor by the corresponding probability multiplier before scaling the density curves.

The probability curves are calculated in sample calibration step 102 which follows reference calibration step 100. The sample calibration is performed on a sample frame, which can be the same frame as the reference frame or subsequent frames to the reference frame. While it may be desirable to perform a sample calibration on every frame, it will usually be impractical due to the processing time required by the sample calibration.

Figure 9:
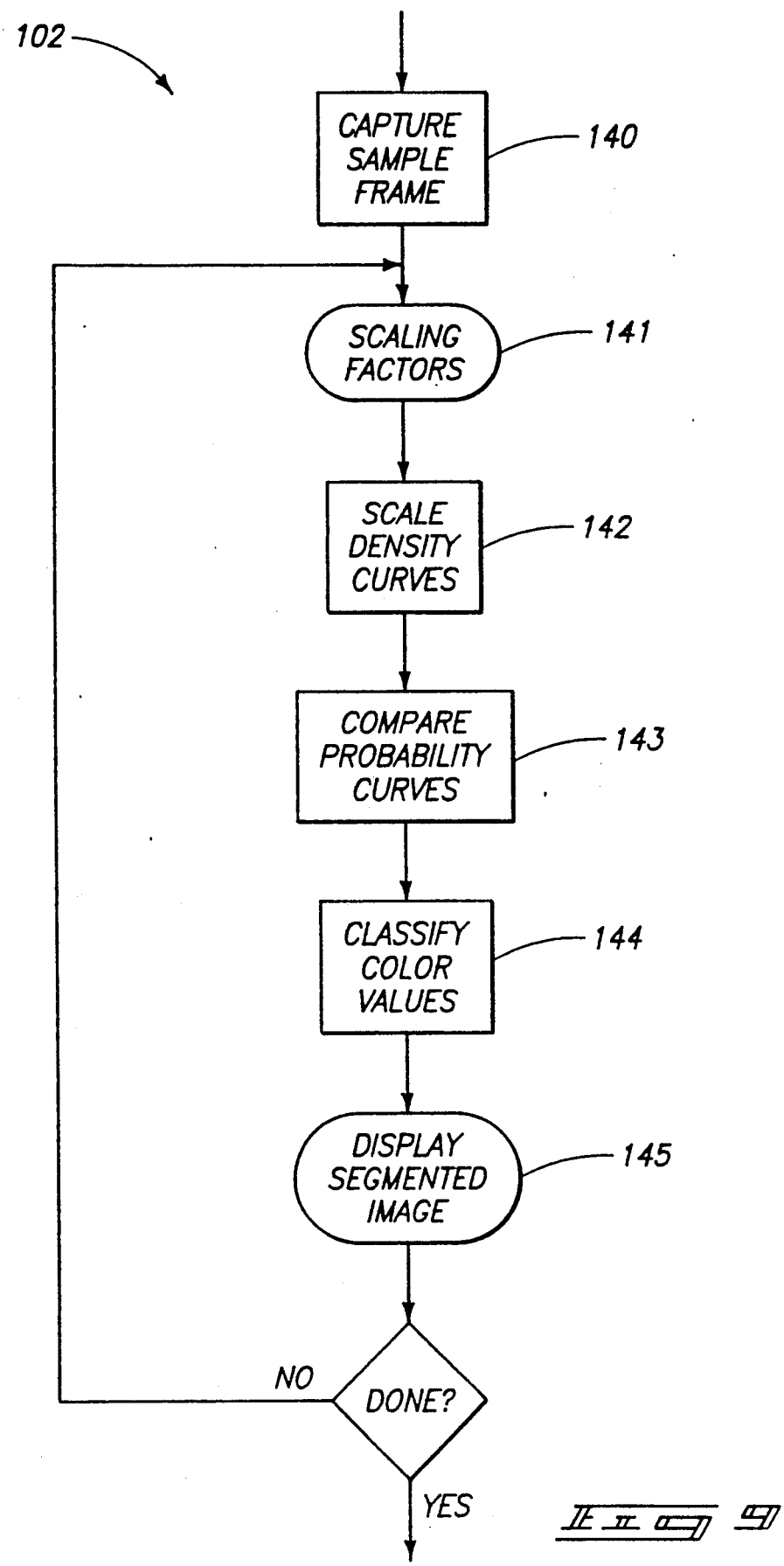
FIG. 9 is a simplified flow chart of a first embodiment sample calibration in accordance with the methods of this invention.

FIG. 9 is a flow chart showing a first embodiment of a sample calibration 102. The sample calibration includes the following steps performed by control system 40: (a) capturing a sample video frame of a product which is to be inspected or segmented (step 140); (b) obtaining scaling factors from an operator (step 141); (c) scaling the density curves (obtained during reference calibration) by the density scaling factors to obtain relative probability curves (step 142); (d) comparing the probability curves at each color value to determine the component type having the highest probability at each color value (step 143); (e) classifying each color value as the component type having the highest relative probability at that color value (step 144); and (f) displaying a segmented representation of the sample video frame (step 145).

The density scaling factors are obtained from the operator. Further, the operator can repetitively adjust the density scaling factors and view the resulting sample frame segmentation. To accomplish this, the sample frame is displayed on graphics display terminal 48 with an indication of segmented areas. Simultaneously, either on the graphics display terminal 48 or on data display terminal 46, operator controls are displayed which allow the operator to set and adjust density scaling factors. As the operator varies the scaling factors, the operator may monitor the effect of the scaling factors on the sample image segmentation. The operator adjusts the scaling factors until the desired or optimal discrimination between component type areas is attained, or until the operator is satisfied with the resulting pixel classifications.

Once the probability curves have been calculated, the pixels of subsequent sample frames are classified or segmented merely by comparing the relative probabilities at the pixels' color values. Alternatively, processing means 42 contains a look-up table for storing the proper color value classifications. The table is loaded during the sample calibration for later reference while analyzing subsequent sample frames. As another alternative, the probability curves are compared only as needed, when a pixel having a particular color value is being classified, with the results of each comparison being stored in a memory look-up table as the comparison is completed. Using this latter variation, each color value is classified only once, and only when needed. If subsequent pixels have the same color value, reference is made to the look-up table for the proper classification.

Figure 11:
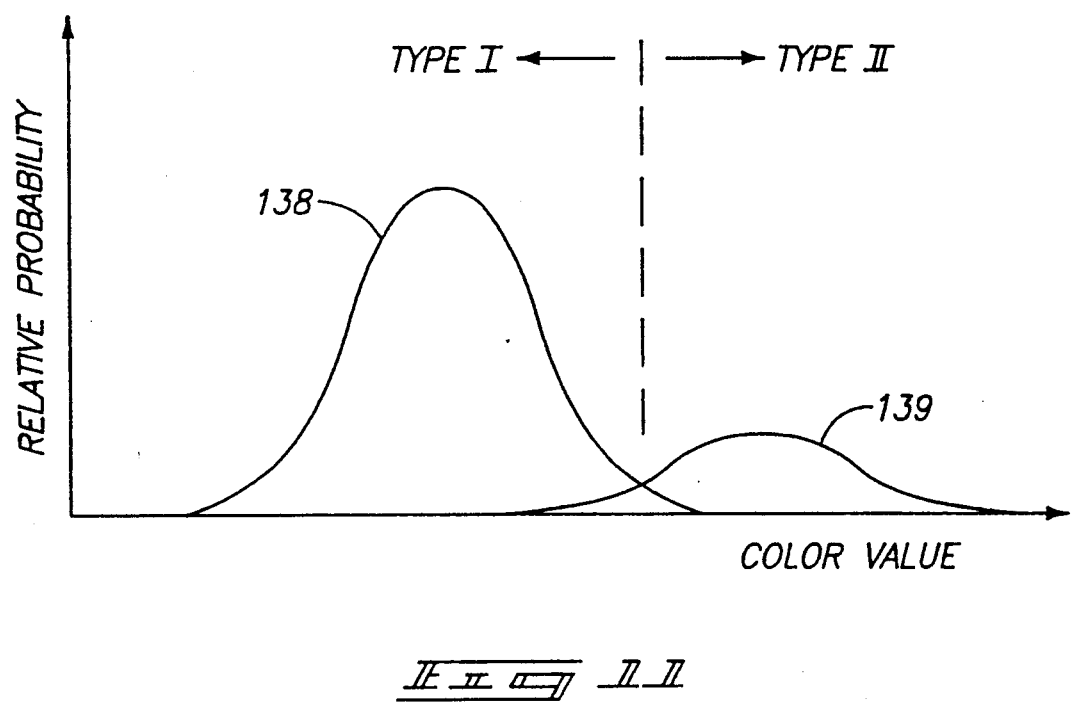
FIG. 11 shows relative probability curves corresponding to the type I and type II areas of FIG. 6.

FIG. 10 shows reference curves 136 and 137 acquired during the reference calibration. FIG. 11 shows the corresponding probability curves 138 and 139 obtained by scaling reference curves 136 and 137. The classification of pixels, based on their color values, is performed by reference to the probability curves. At an individual pixel's color value, the probability types for each component value are compared to determine which has the highest value. The pixel is classified as the component type having the highest probability at the pixel's color value. In the simplified, single-dimensional situation illustrated, all color values to the left of the intersection of the two probability curves will be classified as type I component elements. All color values to the right of the intersection of the two probability curves will be classified as type II component elements. Increasing the scaling factor for component type II will result in the intersection moving to the left, thereby increasing the number of color values which are classified as type II.

In actual practice, the color values occupy a three-dimensional space. While varying one component type's scaling factor increases the number of color values which will be classified as that component type, it does not have the effect of varying a simple threshold. Rather, the color values of each component type are represented by an irregular three-dimensional shape which expands and contracts as the corresponding scaling factor is adjusted. While this shape cannot be conveniently viewed on a display monitor, the resulting segmentation can, as illustrated by FIG. 12.

Figure 12:
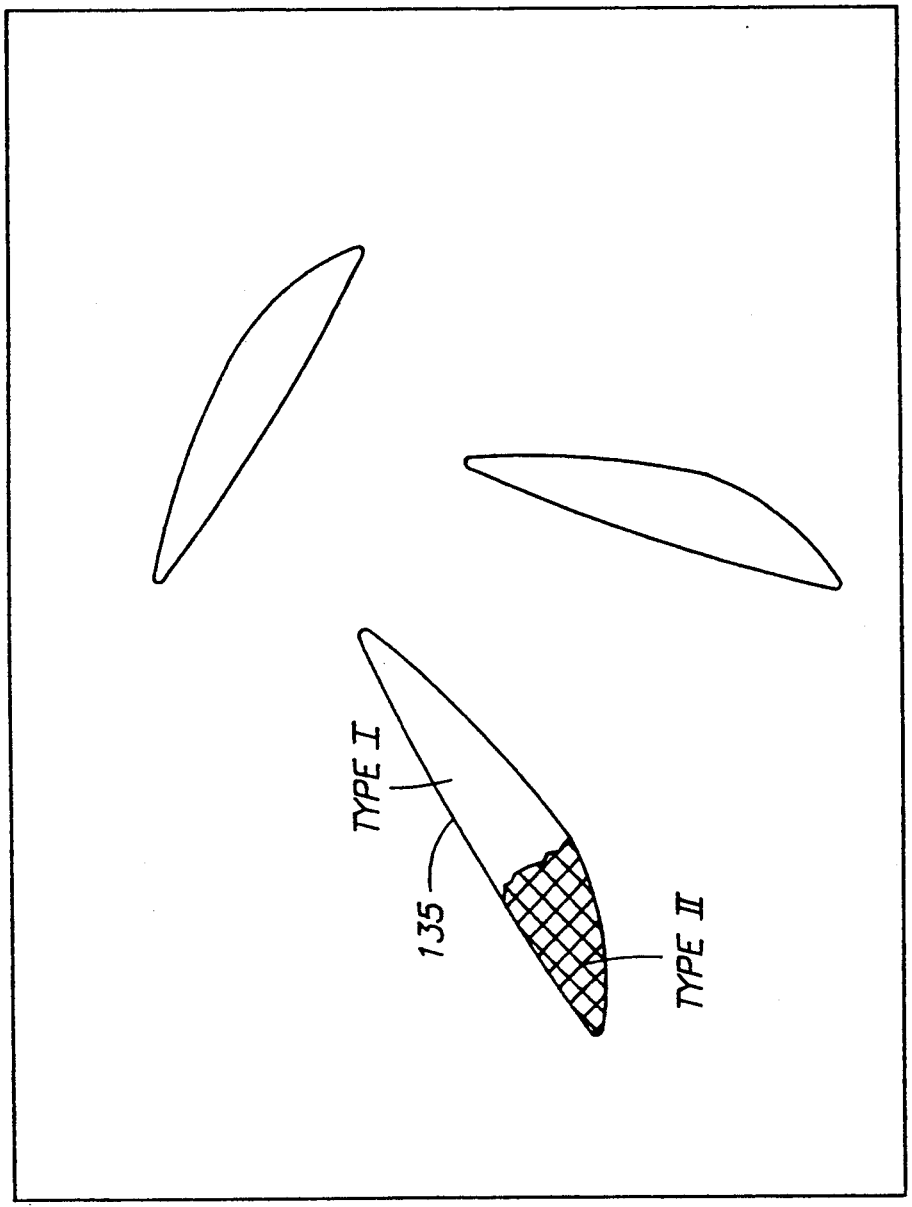
FIG. 12 illustrates a segmented sample video frame.

FIG. 12 illustrates a segmented sample video frame 149. Each image is segmented according to the component type classifications of its pixels' color values, with a representation of the segmented image being displayed on graphics display monitor 48. The displayed segmented representations are updated in response to the operator providing new scaling factors. Therefore, the operator need only adjust the various component type scaling factors to provide the desired results, based on the segmented image displayed on the video display monitor.

Figure 13:
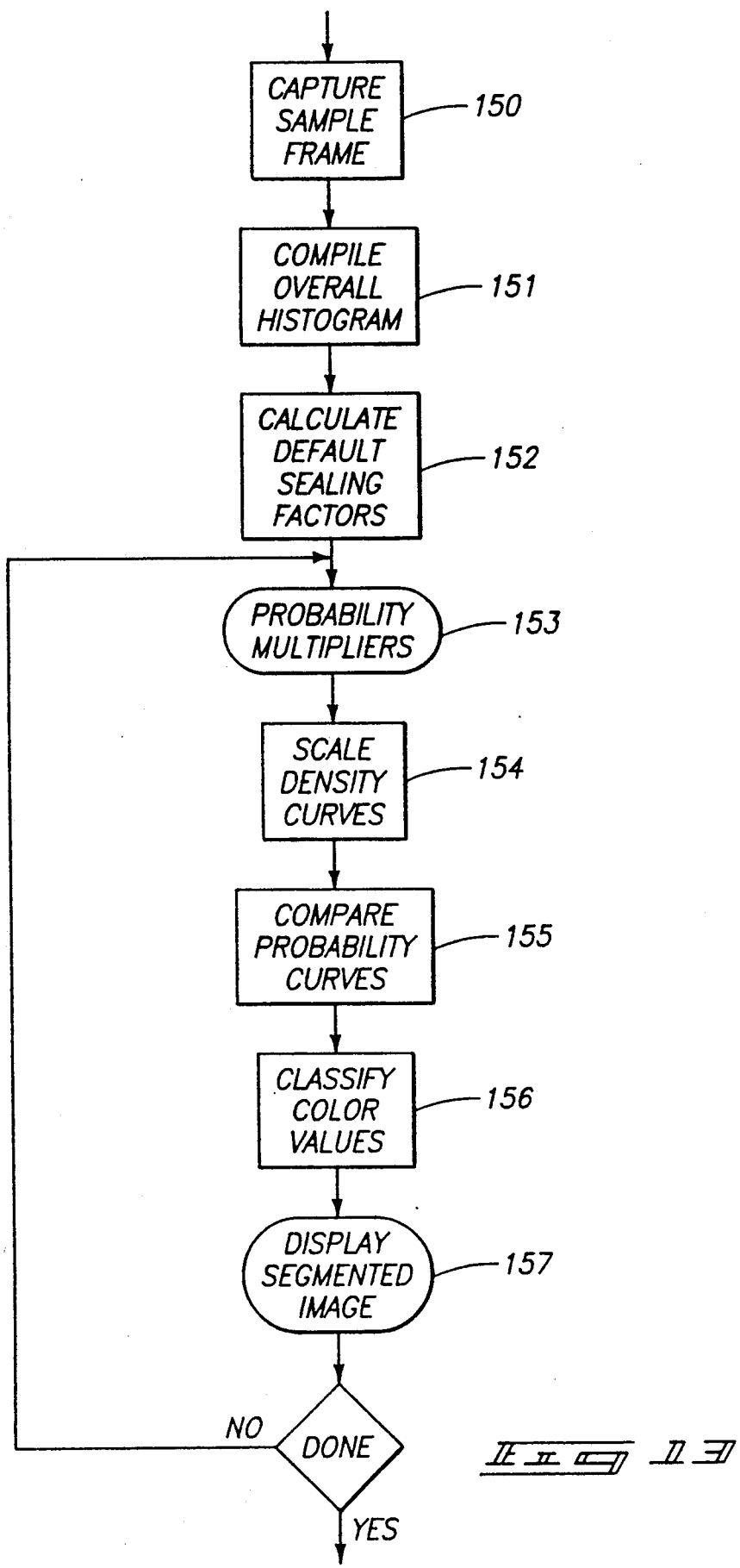
FIG. 13 is a simplified flow chart of a second embodiment sample calibration in accordance with the methods of this invention.

FIG. 13 illustrates a second preferred form of sample calibration step 102. The sample calibration includes the following steps performed by control system 40: (a) capturing a sample video frame of a product which is to be inspected or segmented (step 150); (b) compiling an overall histogram of color values within the entire sample video frame, or at least a major portion thereof (step 151); (c) comparing the density curves (obtained during reference calibration) to the overall histogram to obtain scaling factors corresponding to each density curve (step 152); (d) obtaining probability multipliers from an operator (step 153); (e) adjusting the density scaling factors by the probability multipliers (step 154); (f) scaling the density curves by the adjusted scaling factor to obtain probability reference curves corresponding to the component types (step 155); (g) comparing the probability curves at each color value to determine the component type having the highest probability at each color value (step 156); (h) classifying each color value as the component type having the highest relative probability at that color value (step 157); and (i) displaying a segmented representation of the sample video frame (step 158).

Figure 14:
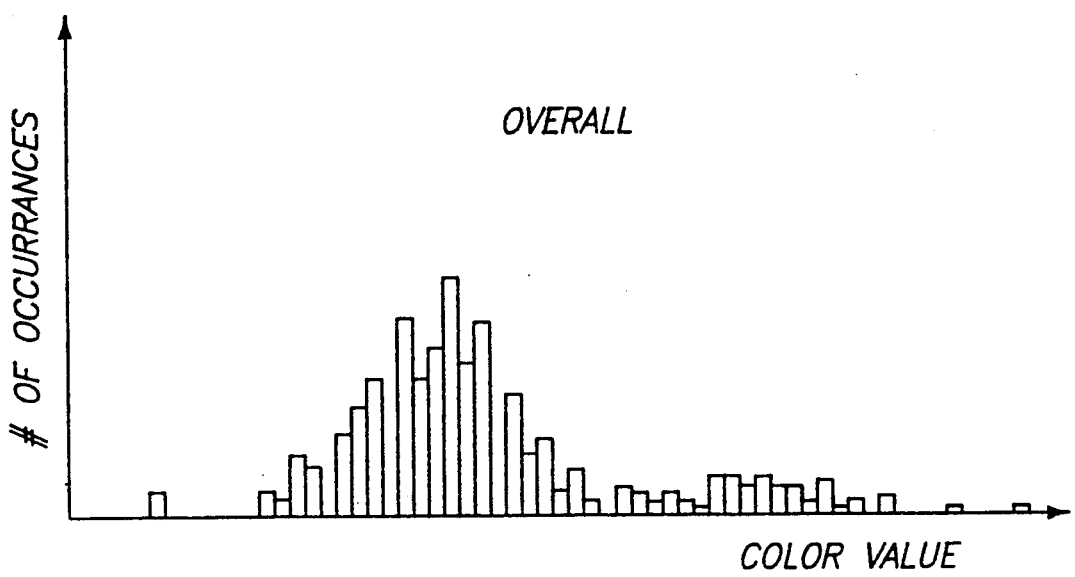
FIG. 14 is an overall histogram of color values occurring within the entire video frame of FIG. 6.

FIG. 14 shows an overall histogram corresponding to a sample video frame. The overall histogram indicates the number of occurrences of each possible color value within the sample frame. In general, an overall histogram will include peaks which correspond to the peaks of the individual reference curves.

Default density scaling factors are computed by comparing the density curves to the overall histogram. This comparison can take various forms, with the object being to find scaling factors which transform the reference curves into relative probability curves, wherein the curves are meaningful in comparison to each other. One comparison includes determining a continuous overall distribution function for the overall histogram and then scaling each reference curve so that its peak has a magnitude equal to the corresponding magnitude of the overall distribution function.

A less computation intensive method computes each scaling factor by summing the product of the corresponding density curve and the overall histogram over a range of color values. Thus, the scaling factor K for component type T is determined by the following equation:

Component Scaling Factor $K_T$:

$$K_T = \sum_{r=0}^{l} \sum_{g=0}^{m} \sum_{b=0}^{n} D_T(r,g,b) \, H_O(r,g,b)$$

where $H_O(r,g,b)$ is the overall histogram, representing the number of occurrences of color values defined by red (r), green (g), and blue (b) intensities; and $D_T(r,g,b)$ represents the reference curve for component type T. "l," "m," and "n" are the highest allowable intensities allowed for red, green, and blue, respectively. This method of scaling has been found to provide reliable scaling factors, and can be performed without operator intervention.

Default scaling factors can be adjusted if desired. Processor 42 obtains probability multipliers corresponding to each component type from the operator. The default density scaling factors are adjusted by the probability multipliers prior to the scaling step.

The sample image is then segmented according to the component type classifications of its color values, with a representation of the segmented image being displayed on graphics display monitor 48. The displayed segmented representations are updated in response to the operator providing new probability multipliers. Therefore, the operator need only adjust the various component type probability multipliers to provide the desired results, based on the segmented sample frame displayed on the graphics display monitor.

The calibration step described above can be performed for every sample frame, processing speed permitting. No operator intervention is required since the operator adjustments are applied proportionally to each succeeding sample frame according to the percentages specified. Normally, however, time and processing speed constraints will preclude sample calibrations except at rather lengthy intervals.

Classification of pixels is performed as already described with reference to FIG. 11. In practice, control system 40 compares the probability at each color value prior to classifying pixels, with the resulting color value classification being stored in a three-dimensional look-up table. As individual pixels are processed, the processor refers to the look-up table for the proper classification.

FIG. 15 shows an alternative method of reference frame calibration 100. The alternative reference frame calibration method initially follows the steps discussed with reference to FIG. 5. However, the alternative method is reiterative. After performing steps 120–124, a sample calibration 102 is performed, with the reference frame as the sample frame, in accordance with the procedures already discussed. The sample calibration 102 is used as an alternative form of component selection, with the resulting segmented areas being used as component type areas while repeating steps 123 and 124.

Using this alternative reference frame calibration method, the operator need initially only define a very small area for each component type. The pixels in this small area are then analyzed to create a first approximation of the desired classification. The operator adjusts scaling factors or probability multipliers to define larger component areas in the reference frame, with these larger areas being subsequently used in obtaining revised reference histograms and density curves, and more accurate classifications.

The methods described above can be integrated in an online sorting machine such as described in U.S. Pat. No. 4,581,632, entitled "Optical Inspection Apparatus for Moving Articles." Such a sorting machine has a line scan camera which views articles as they pass beneath on a conveyor belt. The machine includes processing means for classifying individual pixels and for then identifying and rejecting defective products based on the pixel classification. High classification speeds are attained by loading color value classification data in a look-up table. Improved control over classification parameters can be achieved by utilizing the methods described above in loading the table.

The classifications and quality control parameters obtained through the above methods can also be used to set and adjust process parameters of other in-line processing equipment such as blanchers, steam peelers, etc.

In compliance with the statute, the invention has been described in language more or less specific as to structural and methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An automated quality inspection device for evaluating optical component characteristics of a product, the inspection device comprising:
    means for capturing video frames of product images, each video frame comprising an array of color values, each color value being specified by at least one variable;

component selection means for allowing an operator to identify portions of individual component types within a reference video frame;

control means for (1) deriving relative component type probability curves from the identified portions of the individual component types, and (2) classifying individual color values as single component types according to the highest relative component type probability for each individual color value;

wherein the control means includes processing means for deriving the relative component type probability curves by comparing color values of the identified portions of component types to the color values of an overall sample video frame.

2. The quality inspection device of claim 1, wherein each color value is specified by at least two variables.

3. The quality inspection device of claim 1, wherein the control means includes a look-up table for storing the component type classifications of individual color values.

4. The quality inspection device of claim 3, further comprising means for displaying segmented representations of the product images, wherein each image is segmented according to the component type classifications of its color values.

5. An automated quality inspection device for evaluating optical component characteristics of a product, the inspection device comprising:

means for capturing video frames of product images, each video frame comprising an array of color values, each color value being specified by at least one variable;

component selection means for allowing an operator to identify portions of individual component types within a reference video frame;

control means for (1) deriving relative component type probability curves from the identified portions of the individual component types, and (2) classifying individual color values as single component according to the highest relative component type probability for each individual color value;

wherein the control means includes processing means for:

compiling reference histograms of color values occurring within the identified portions of the reference video frame;

calculating color value density curves from the reference histograms; and scaling the density curves by scaling factors to obtain the relative component type probability curves.

6. The quality inspection device of claim 5, wherein the control means includes a look-up table for storing the component type classifications of individual color values.

7. The quality inspection device of claim 5, further comprising means for obtaining the scaling factors from an operator.

8. The quality inspection device of claim 5, further comprising:

means for obtaining the scaling factors from an operator; and means for displaying segmented representations of a sample video frame to the operator;

processing means for segmenting the sample video frame according to the component type classifications of its color values, the displayed segmented representations being updated in response to the operator providing new scaling factors.

9. The quality inspection device of claim 5, wherein the control means includes processing means for calculating the density curves by fitting a continuous function to each reference histogram.

10. The quality inspection device of claim 5, wherein the control means includes processing means for calculating the density curves by fitting a set of gaussian-weighted Hermite polynomials to each reference histogram.

11. An automated quality inspection device for evaluating optical component characteristics of a product, the inspection device comprising:

means for capturing video frames of product images, each video frame comprising an array of color values, each color value being specified by at least one variable;

component selection means for allowing an operator to identify portions of individual component types within a reference video frame;

control means for (1) deriving relative component type probability curves from the identified portions of the individual component types, and (2) classifying individual color values as single component types according to the highest relative component type probability for each individual color value;

wherein the control means has processing means for:

compiling reference histograms of color values occurring within the identified portions of the reference video frame;

calculating color value density curves from the reference histograms;

compiling an overall histogram of color values within a sample video frame;

comparing the density curves to the overall histogram to obtain a scaling factor corresponding to each density curve; and scaling the density curves by the scaling factors to obtain the relative component type probability curves.

12. The quality inspection device of claim 11, further comprising:

means for obtaining probability multipliers corresponding to the relative probability curves from an operator;

the processing means being further for adjusting each density scaling factor by the corresponding probability multiplier before scaling the density curves.

13. The quality inspection device of claim 11, wherein the processing means includes a look-up table for storing the component type classifications of individual color values.

14. The quality inspection device of claim 11, wherein the processing means calculates the density curves by fitting a set of gaussian-weighted Hermite polynomials to each reference histogram.

15. The quality inspection device of claim 11, further comprising:

means for obtaining probability multipliers from an operator;

the processing means being further for adjusting each density scaling factor by the corresponding probability multiplier before scaling the density curves; and means for displaying segmented representations of the sample video frame to the operator, wherein the sample frame is segmented according to the component type classifications of its color values, the segmented representations being updated in response to the operator providing new probability multipliers.

16. The quality inspection device of claim 11, wherein the control means obtains each scaling factor by summing the product of the corresponding density curve and the overall histogram over a range of color values.

17. The quality inspection device of claim 16, further comprising means for obtaining probability multipliers corresponding to the relative probability curves from an operator, the processing means being further for adjusting each density scaling factor by the corresponding probability multiplier before scaling the density curves.

18. An automated color component classification device for identifying component types in a sample product having a plurality of component types, the inspection device comprising:
   a sample surface for supporting product which is to be inspected;
   a camera positioned relative to the optical inspection surface to produce video flames of the supported sample product, each video frame containing an array of pixels, wherein each pixel has an associated color value which is specified by at least two variables;
   a video display monitor which displays video frames to an operator;
   component selection means for allowing an operator to identify portions of individual component types within a reference video frame;
   a data processor operably connected to the camera, the video display monitor, and the component selection means, the data processor being programmed to derive relative component type probability curves from the identified portions of the individual component types, and to classify individual color values as single component types according to the highest relative component type probability for each color value;
   wherein the data processor is programmed to derive the relative component type probability curves by comparing color values of the identified portions of component types to the color values of an overall sample video frame.

19. The component classification device of claim 18, further comprising a memory look-up table for storing the component type classifications of individual color values.

20. The component classification device of claim 19, further comprising means for displaying segmented sample video frames, wherein each sample video frame is segmented according to the component type classifications of its color values.

21. An automated color component classification device for identifying component types in a sample product having a plurality of component types, the inspection device comprising:
   a sample surface for supporting product which is to be inspected;
   a camera positioned relative to the optical inspection surface to produce video frames of the supported sample product, each video frame containing an array of pixels, wherein each pixel has an associated color value which is specified by at least two variables;
   a video display monitor which displays video frames to an operator;
   component selection means for allowing an operator to identify portions of individual component types within a reference video frame;
   a data processor operably connected to the camera, the video display monitor, and the component selection means, the data processor being programmed to derive relative component type probability curves from the identified portions of the individual component types, and to classify individual color values as single component types according the highest relative component type probability for each color value;
   wherein the data processor is further programmed to:
   compile reference histograms of color values occurring within the identified portions of the reference video frame;
   calculate color value density curves from the reference histograms; and
   scale the density curves by scaling factors to obtain the relative component type probability curves.

22. The component classification device of claim 21, further comprising a memory look-up table for storing the component type classifications of individual color values.

23. The component classification device of claim 21, further comprising means for obtaining the scaling factors from an operator.

24. The component classification device of claim 21, further comprising:
   means for obtaining the scaling factors from an operator; and
   means for displaying segmented representations of sample video frames;
   wherein the sample video frame is segmented according to the component type classifications of its color values, the displayed segmented representations being updated in response to the operator providing new scaling factors.

25. The component classification device of claim 21, wherein the data processor calculates the density curves by fitting a set of gaussian-weighted Hermite polynomials to each reference histogram.

26. An automated color component classification device for identifying Component types in a sample product having a plurality of component types, the inspection device comprising:
   a sample surface for supporting product which is to be inspected;
   a camera positioned relative to the optical inspection surface to produce video frames of the supported sample product, each video frame containing an array of pixels, wherein each pixel has an associated color value which is specified by at least two variables;
   a video display monitor which displays video frames to an operator;
   component selection means for allowing an operator to identify portions of individual component types within a reference video frame;
   a data processor operably connected to the camera, the video display monitor, and the component selection means, the data processor being programmed to derive relative component type probability curves from the identified portions of the individual component types, and to classify individual color values as single component types according the highest relative component type probability for each color value;

wherein the data processor is further programmed to:
compile reference histograms of color values occurring within the identified portions of the reference video frame;
calculate color value density curves from the reference histograms;
compile an overall histogram of color values within a sample video frame;
compare the density curves to the overall histogram to obtain a scaling factor corresponding to each density curve; and
scale the density curves by the scaling factors to obtain the relative component type probability curves.

27. The component classification device of claim 26, further comprising:
means for obtaining probability multipliers corresponding to the relative probability curves from an operator;
the data processor being further programmed to adjust each density scaling factor by the corresponding probability multiplier before scaling the density curves.

28. The component classification device of claim 26, further comprising a memory look-up table for storing the component type classifications of individual color values.

29. The component classification device of claim 26, wherein the data processor calculates the density curves by fitting a set of gaussian-weighted Hermite polynomials to each reference histogram.

30. The component classification device of claim 26, further comprising:
means for obtaining probability multipliers from an operator;
the data processor being further programmed to adjust each density scaling factor by the corresponding probability multiplier before scaling the density curves; and
means for displaying segmented representations of the sample video frame to the operator, wherein the sample video frame is segmented according to the component type classifications of its color values, the segmented representations being updated in response to the operator providing new probability multipliers.

31. The component classification device of claim 26, wherein the data processor is programmed to obtain each scaling factor by summing the product of the corresponding density curve and the overall histogram over a range of color values.

32. The component classification device of claim 31, further comprising means for obtaining probability multipliers corresponding to the relative probability curves from an operator, the data processor being further programmed to adjust each density scaling factor by the corresponding probability multiplier before scaling the density curves.

33. An automated quality inspection device for evaluating color component characteristics of a product, the inspection device comprising:
an optical transducer which produces a video signal representative of color characteristics of the product;
a frame grabber which receives the video signal and captures video frames representing images of the product, each video frame containing an array of pixels, each pixel having an associated color value which is specified by at least two variables;
a video display upon which a reference video frame is displayed to an operator;
component selection means for allowing the operator to identify portions of component type areas from the displayed reference video frame;
a data processor operably connected to read pixel color values from the frame grabber and programmed to:
(a) compile reference histograms of color values within the identified portions of the reference frame component type areas;
(b) calculate color value density curves from the reference histograms;
(c) calibrate the density curves relative to each other;
(d) classify an individual pixel as the component type having the highest calibrated density curve value at the color value of the individual pixel;
wherein the data processor is programmed to calibrate the density curves by comparing them to an overall histogram of the color values occurring within an overall sample video frame.

34. The quality inspection device of claim 33, wherein the data processor includes a look-up table for storing component type classifications of individual color values.

35. An automated quality inspection device for evaluating color component characteristics of a product, the inspection device comprising:
an optical transducer which produces a video signal representative of color characteristics of the product;
a frame grabber which receives the video signal and captures video frames representing images of the product, each video frame containing an array of pixels, each pixel having an associated color value which is specified by at least two variables;
a video display upon which a reference video frame is displayed to an operator;
component selection means for allowing the operator to identify portions of component type areas from the displayed reference video frame;
a data processor operably connected to read pixel color values from the frame grabber and programmed to:
(a) compile reference histograms of color values within the identified portions of the reference frame component type areas;
(b) calculate color value density curves from the reference histograms;
(c) calibrate the density curves relative to each other;
(d) classify an individual pixel as the component type having the highest calibrated density curve value at the color value of the individual pixel;
wherein the data processor is programmed to calibrate the density curves by scaling each density curve by an operator-supplied scaling factor.

36. An automated quality inspection device for evaluating color component characteristics of a product, the inspection device comprising:
an optical transducer which produces a video signal representative of color characteristics of the product;
a frame grabber which receives the video signal and captures video frames representing images of the product, each video frame containing an array of pixels, each pixel having an associated color value which is specified by at least two variables;

a video display upon which a reference video frame is displayed to an operator;

component selection means for allowing the operator to identify portions of component type areas from the displayed reference video frame;

a data processor operably connected to read pixel color values from the frame grabber and programmed to:

(a) compile reference histograms of color values within the identified portions of the reference frame component type areas;

(b) calculate color value density curves from the reference histograms;

(c) calibrate the density curves relative to each other;

(d) classify an individual pixel as the component type having the highest calibrated density curve value at the color value of the individual pixel;

means for obtaining scaling factors from an operator;

wherein the data processor is programmed to calibrate the density curves by scaling the density curves by the scaling factors; and wherein the data processor is programmed to display segmented representations of sample video frames on the video display, each sample video frame being segmented according to the component type classifications of its pixels, the data processor being programmed to update the displayed segmented representations in response to the operator providing new scaling factors.

37. An automated quality inspection device for evaluating color component characteristics of a product, the inspection device comprising:

an optical transducer which produces a video signal representative of color characteristics of the product;

a frame grabber which receives the video signal and captures video frames representing images of the product, each video frame containing an array of pixels, each pixel having an associated color value which is specified by at least two variables;

a video display upon which a reference video frame is displayed to an operator;

component selection means for allowing the operator to identify portions of component type areas from the displayed reference video frame;

a data processor operably connected to read pixel color values from the frame grabber and programmed to:

(a) compile reference histograms of color values within the identified portions of the reference frame component type areas;

(b) calculate color value density curves from the reference histograms;

(c) calibrate the density curves relative to each other;

(d) classify an individual pixel as the component type having the highest calibrated density curve value at the color value of the individual pixel;

wherein the data processor is programmed to calculate the density curves by fitting a set of gaussian-weighted Hermite polynomials to each reference histogram.

38. An automated quality inspection device for evaluating color component characteristics of a product, the inspection device comprising:

an optical transducer which produces a video signal representative of color characteristics of the product;

a frame grabber which receives the video signal and captures video frames representing images of the product, each video frame containing an array of pixels, each pixel having an associated color value which is specified by at least two variables;

a video display upon which a reference video frame is displayed to an operator;

component selection means for allowing the operator to identify portions of component type areas from the displayed reference video frame;

a data processor operably connected to read pixel color values from the frame grabber and programmed to:

(a) compile reference histograms of color values within the identified portions of the reference frame component type areas;

(b) calculate color value density curves from the reference histograms;

(c) calibrate the density curves relative to each other;

(d) classify an individual pixel as the component type having the highest calibrated density curve value at the color value of the individual pixel;

wherein the data processor is programmed to calibrate the density curves by:

compiling an overall histogram of color values within a sample video frame;

comparing the density curves to the overall histogram to obtain a density scaling factor corresponding to each density curve; and scaling the density curves by their corresponding density scaling factors to obtain corresponding relative probability curves which represent the probability of any single color value occurring in any single component type relative to any other component types.

39. The quality inspection device of claim 38, further comprising:

means for obtaining probability multipliers corresponding to the relative probability curves from an operator;

the data processor being further programmed to adjust each density scaling factor by the corresponding probability multiplier before scaling the density curves.

40. The quality inspection device of claim 38, wherein the data processor includes a look-up table for storing component type classifications of individual color values.

41. The quality inspection device of claim 38, wherein the data processor is programmed to calculate the density curves by fitting a set of gaussian-weighted Hermite polynomials to each reference histogram.

42. The quality inspection device of claim 38, further comprising:

means for obtaining probability multipliers from an operator; and means for displaying segmented representations of a sample video frame to the operator, wherein the sample video frame is segmented according to the component type classifications of its color values, the segmented representations being updated in response to the operator providing new probability multipliers.

43. The quality inspection device of claim 38, wherein the data processor is programmed to obtain each density scaling factor by summing the product of the corresponding density curve and the overall histogram over a range of color values.

44. The quality inspection device of claim 43, further comprising means for obtaining probability multipliers corresponding to the relative probability curves from an operator, the data processor being programmed to adjust each density scaling factor by the corresponding probability multiplier before scaling the density curves.

45. A method of classifying video pixels in a product inspection device as one of a plurality of component types, wherein each pixel has an associated color value, each color value being specified by at least one variable, the method comprising the following steps:
   capturing a reference video frame of a product image, the reference video frame comprising an array of video pixels;
   identifying portions of individual component types within the reference video frame;
   deriving relative component type probability curves from the identified portions of the individual component types; and
   classifying individual pixels as single component types according to the highest relative component type probability for each individual pixel's color value;
   wherein the step of deriving the relative component type. probability curves comprises comparing color values of the identified portions of component types to the color values of an overall sample video frame.

46. The method of claim 45, wherein each color value is specified by at least two variables.

47. The method of claim 45, further comprising the following additional steps:
   classifying individual color values as individual component types according to their highest relative probability; and
   storing the component type classifications of individual color values in a look-up table.

48. The method of claim 45, further comprising the following additional steps:
   segmenting a video frame based on the classifications of its pixels; and
   displaying the segmented video frame.

49. A method of classifying video pixels in a product inspection device as one of a plurality of component types, wherein each pixel has an associated color value, each color value being specified by at least one variable, the method comprising the following steps:
   capturing a reference video frame of a product image, the reference video frame comprising an array of video pixels;
   identifying portions of individual component types within the reference video frame;
   deriving relative component type probability curves from the identified portions of the individual component types;
   classifying individual pixels as single component types according to the highest relative component type probability for each individual pixel's color value;
   compiling reference histograms of color values occurring within the identified portions of the reference video frame;
   calculating color value density curves from the reference histograms; and
   scaling the density curves by scaling factors to obtain the relative component type probability curves.

50. The method of claim 49, further comprising the following additional steps:
   classifying individual color values as individual component types according to their highest relative probability; and
   storing the component type classifications of individual color values in a look-up table.

51. The method of claim 49, further comprising the additional step of obtaining the scaling factors from an operator.

52. The method of claim 49, further comprising the following additional steps:
   obtaining the scaling factors from an operator;
   segmenting the video frame based on the classifications of its pixels;
   displaying the segmented video frame; and
   updating the segmented video frame display in response to the operator providing new scaling factors.

53. The method of claim 49, wherein the step of calculating color value density curves from the reference histograms comprises fitting a set of gaussian-weighted Hermite polynomials to each reference histogram.

54. A method of classifying video pixels in a product inspection device as one of a plurality of component types, wherein each pixel has an associated color value, each color value being specified by at least one variable, the method comprising the following steps:
   capturing a reference video frame of a product image, the reference video frame comprising an array of video pixels;
   identifying portions of individual component types within the reference video frame;
   deriving relative component type .probability curves from the identified portions of the individual component types;
   classifying individual pixels as single component types according to the highest relative component type probability for each individual pixel's color value;
   compiling reference histograms of color values occurring within the identified portions of the reference video frame;
   calculating color value density curves from the reference histograms;
   compiling an overall histogram of color values within a sample video frame;
   comparing the density curves to the overall histogram to obtain a scaling factor corresponding to each density curve; and
   scaling the density curves by scaling factors to obtain the relative component type probability curves.

55. The method of claim 54, further comprising the following additional steps:
   obtaining probability multipliers corresponding to the relative probability curves from an operator; and
   adjusting each density scaling factor by the corresponding probability multiplier before scaling the density curves.

56. The method of claim 54, further comprising the following additional steps:
   classifying individual color values as individual component types according to their highest relative probability; and storing the component type classifications of individual color values in a look-up table.

57. The method of claim 54, wherein the step of calculating color value density curves from the reference histograms comprises fitting a set of gaussian-weighted Hermite polynomials to each reference histogram.

58. The method of claim 54, further comprising the following additional steps:
obtaining probability multipliers corresponding to the relative probability curves from an operator;
adjusting each density scaling factor by the corresponding probability multiplier before scaling the density curves;
segmenting the sample video frame based on the classifications of its pixels;
displaying the segmented video frame; and
updating the segmented video frame display in response to the operator providing new probability multipliers.

59. The method of claim 54, wherein the step of comparing the density curves to the overall histogram comprises summing the product of the corresponding density curve and the overall histogram over a range of color values.

60. The method of claim 59, further comprising the following additional steps:
obtaining probability multipliers corresponding to the relative probability curves from an operator;
adjusting each density scaling factor by the corresponding probability multiplier before scaling the density curves.

* * * * *